United States Patent
Iwase et al.

(10) Patent No.: US 10,383,511 B2
(45) Date of Patent: Aug. 20, 2019

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Yoshihiko Iwase, Yokohama (JP); Akihiro Katayama, Zama (JP)

(73) Assignee: Canon Kabushiki Kaisha, Tokyo (JP)

( * ) Notice: Subject to any disclaimer, the term of this patent is extended or adjusted under 35 U.S.C. 154(b) by 136 days.

(21) Appl. No.: 14/028,692

(22) Filed: Sep. 17, 2013

(65) Prior Publication Data
US 2014/0016096 A1  Jan. 16, 2014

Related U.S. Application Data

(63) Continuation of application No. 13/319,879, filed as application No. PCT/JP2010/060919 on Jun. 21, 2010, now Pat. No. 8,556,424.

(30) Foreign Application Priority Data

Jul. 14, 2009  (JP) .................................. 2009-166181

(51) Int. Cl.
*A61B 3/14* (2006.01)
*A61B 3/00* (2006.01)
(Continued)

(52) U.S. Cl.
CPC .......... *A61B 3/0058* (2013.01); *A61B 3/0025* (2013.01); *A61B 3/102* (2013.01);
(Continued)

(58) Field of Classification Search
CPC ..... A61B 3/0025; A61B 3/102; A61B 3/1225; A61B 3/0058; A61B 3/024; A61B 3/085; A61B 3/10; A61B 3/112; A61B 3/113; A61B 3/117; A61B 3/1005; A61B 5/0059; A61B 5/0066; A61B 5/0073; A61B 5/748;
(Continued)

(56) References Cited

U.S. PATENT DOCUMENTS

| 6,293,674 | B1 * | 9/2001 | Huang .................. A61B 3/102 |
| | | | 351/221 |
| 7,510,282 | B2 | 3/2009 | Ueno et al. |

(Continued)

FOREIGN PATENT DOCUMENTS

| CN | 101204318 A | 6/2008 |
| CN | 101251365 A | 8/2008 |

(Continued)

OTHER PUBLICATIONS

May 26, 2014 Chinese Official Action in Chinese Patent Appln. No. 201080031755.8.

(Continued)

*Primary Examiner* — Mustak Choudhury
(74) *Attorney, Agent, or Firm* — Venable LLP

(57) ABSTRACT

An image processing apparatus has an acquisition unit which acquires a second tomogram related to a first tomogram of an eye to be examined based on position information of an eye fundus of the eye to be examined according to a predetermined rule; and a display control unit which displays the first tomogram and the second tomogram on a display unit.

36 Claims, 12 Drawing Sheets

(51) Int. Cl.
*A61B 3/10* (2006.01)
*A61B 3/12* (2006.01)
*G06T 7/00* (2017.01)
*G06T 19/00* (2011.01)

(52) U.S. Cl.
CPC .......... *A61B 3/1225* (2013.01); *G06T 7/0012* (2013.01); *G06T 19/00* (2013.01); *G06T 2207/10101* (2013.01); *G06T 2207/30041* (2013.01); *G06T 2219/008* (2013.01)

(58) Field of Classification Search
CPC ..... A61B 5/7445; G06T 7/0012; G06T 19/00; G06T 2207/10101; G06T 2219/008; G06T 2207/30041; G01B 9/02091; G01B 9/02048; G01B 9/02089; G01B 9/02027
USPC .................. 351/205–247; 382/131; 345/118; 600/558
See application file for complete search history.

(56) References Cited

U.S. PATENT DOCUMENTS

| | | | |
|---|---|---|---|
| 7,566,132 B2 | 7/2009 | Fukuma et al. | |
| 7,794,083 B2 | 9/2010 | Tsukada et al. | |
| 7,980,697 B2 | 7/2011 | Tsukada et al. | |
| 8,474,978 B2 * | 7/2013 | Huang | A61B 3/12 351/246 |
| 8,820,931 B2 * | 9/2014 | Walsh | A61B 3/102 351/206 |
| 2007/0236660 A1 | 10/2007 | Fukuma et al. | |
| 2008/0024721 A1 | 1/2008 | Ueno et al. | |
| 2008/0100612 A1 * | 5/2008 | Dastmalchi | A61B 3/102 345/418 |
| 2008/0151187 A1 | 6/2008 | Tsukada et al. | |
| 2008/0208525 A1 | 8/2008 | Kikawa et al. | |
| 2008/0234972 A1 | 9/2008 | Tsukada et al. | |
| 2008/0309881 A1 | 12/2008 | Huang et al. | |
| 2009/0190092 A1 | 7/2009 | Tsukada et al. | |
| 2009/0237614 A1 * | 9/2009 | Wyatt | A61B 3/112 351/205 |
| 2010/0149489 A1 | 6/2010 | Kikawa et al. | |
| 2010/0189334 A1 | 7/2010 | Tomidokoro et al. | |
| 2010/0238403 A1 * | 9/2010 | Kobayashi et al. | 351/206 |
| 2011/0134392 A1 | 6/2011 | Iwase et al. | |
| 2011/0137157 A1 | 6/2011 | Imamura et al. | |
| 2011/0234785 A1 | 9/2011 | Wanda et al. | |
| 2012/0063660 A1 | 3/2012 | Imamura et al. | |
| 2012/0133950 A1 | 5/2012 | Suehira et al. | |
| 2013/0093998 A1 | 4/2013 | Bishop | |

FOREIGN PATENT DOCUMENTS

| | | | |
|---|---|---|---|
| EP | 1 908 397 A2 | 4/2008 | |
| EP | 2 233 065 A2 | 9/2010 | |
| JP | 2002-032734 A | 1/2002 | |
| JP | 2005-130928 A | 5/2005 | |
| JP | 2007-275374 A | 10/2007 | |
| JP | 2008-029467 A | 2/2008 | |
| JP | 2008-073099 A | 4/2008 | |
| JP | 2008-154704 A | 7/2008 | |
| JP | 2008-209166 A | 9/2008 | |
| JP | 2008-237237 A | 10/2008 | |
| JP | 2008-237238 A | 10/2008 | |
| JP | 2008-289579 A | 12/2008 | |
| JP | 2009-061203 A1 | 3/2009 | |
| JP | 2009-089792 A | 4/2009 | |
| JP | 2009089792 A * | 4/2009 | |
| JP | 2010-529896 A | 9/2010 | |
| WO | 2006/022045 A1 | 3/2006 | |
| WO | 2008/157406 A1 | 12/2008 | |
| WO | 2009/015295 A1 | 1/2009 | |

OTHER PUBLICATIONS

Jul. 20, 2010 International Search Report and Written Opinion in International Application No. PCT/JP2010/060919.
Jan. 13, 2012 Japanese Official Action in Japanese Patent Appln. No. 2011-255427.
Jan. 24, 2013 European Search Report in European Patent Appln. No. 10799717.3.
Office Action in Japanese Application No. 2017-194560, dated Aug. 17, 2018.

* cited by examiner

F I G. 8A
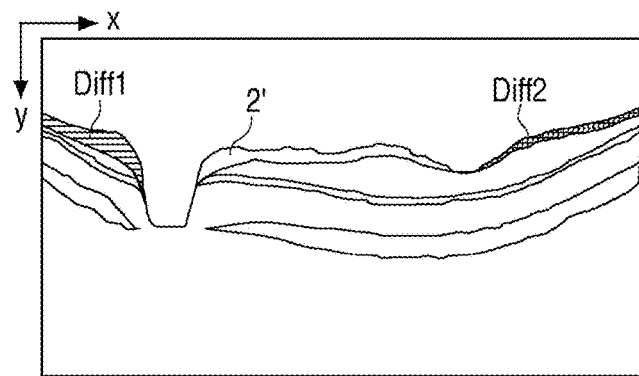
F I G. 8B
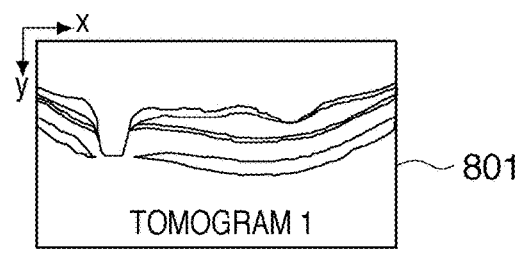
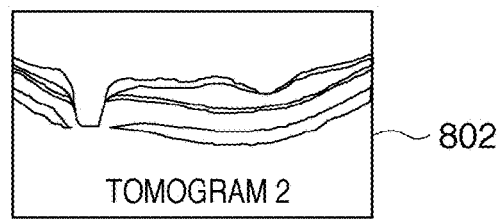
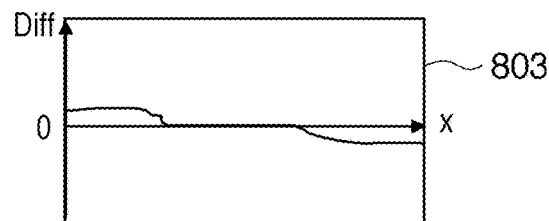
F I G. 8C
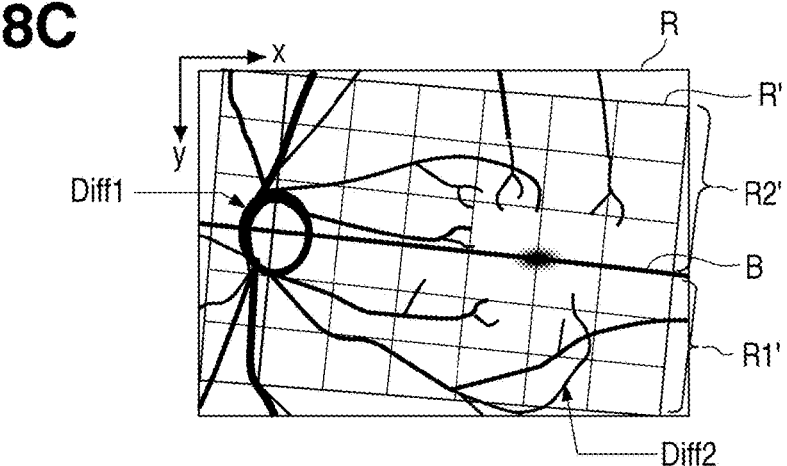

IMAGE PROCESSING APPARATUS, IMAGE PROCESSING METHOD, AND PROGRAM

This application is a continuation of application Ser. No. 13/319,879 filed Nov. 10, 2011, which was the National Stage of International Patent Application No. PCT/JP2010/060919 filed Jun. 21, 2010.

TECHNICAL FIELD

The present invention relates to an image processing technique that assists image processing of an eye portion and, more particularly, to an image processing apparatus, image processing method, and program, which execute image processing using tomograms of an eye portion.

BACKGROUND ART

A tomography apparatus for an eye portion such as an OCT (Optical Coherence Tomography) allows to three-dimensionally observe the state of the interior of retina layers. In recent years, this tomography apparatus for an eye portion has received a lot of attention since it is effective to give more adequate diagnoses of diseases.

FIG. 3A illustrates tomograms of a retina captured by the OCT. Referring to FIG. 3A, reference symbols $T_1$ to $T_n$ denote two-dimensional tomograms (B-scan images) of a macular region. Reference symbol D denotes an optic nerve papilla; and M, a macular region. Reference numeral 1 denotes an inner limiting membrane; 2, a boundary between a nerve fiber layer and its underlying layer (to be referred to as a nerve fiber layer boundary 2 hereinafter); and 2', a nerve fiber layer. Reference numeral 3 denotes a boundary between an inner plexiform layer and its underlying layer (to be referred to as an inner plexiform layer boundary 3 hereinafter); and 4, a boundary between an outer plexiform layer and its underlying layer (to be referred to as an outer plexiform layer boundary 4 hereinafter). Reference numeral 5 denotes a junction between inner and outer photoreceptor segments; 6, a retinal pigment epithelial layer boundary; and 6', a retinal pigment epithelial layer edge. For example, when such tomograms are input, if the thickness (TT1 in FIG. 3A) of the nerve fiber layer 2' can be measured, a degree of progress of a disease such as glaucoma and a recovery level after a medical treatment can be quantitatively diagnosed. In order to judge the progress states and recovery levels of medial treatment effects of diseases of an eye portion, a technique which facilitates comparison operations using a display mode that allows an operator to recognize the mutual relationship between a fundus image and tomograms obtained by the OCT has been disclosed (see Japanese Patent Laid-Open No. 2008-073099).

However, Japanese Patent Laid-Open No. 2008-073099 described above displays an OCT tomogram and layer boundaries corresponding to a position designated on a fundus image, but it merely displays a tomogram and its boundaries at a position designated by a doctor. For this reason, the doctor may often dither to judge about whether a portion having an abnormal layer thickness in the tomogram at the designated position is caused by an individual feature or a disease.

SUMMARY OF INVENTION

According to one aspect of the present invention, there is provided an image processing apparatus comprising: acquisition means for acquiring a second tomogram related to a first tomogram of an eye to be examined based on position information of an eye fundus of the eye to be examined according to a predetermined rule; and display control means for displaying the first tomogram and the second tomogram on display means.

According to the present invention, a plurality of tomograms at structurally symmetric positions in a single eye to be examined are generated, and are displayed to be juxtaposed in a comparable state. Thus, the operator can easily judge whether information obtained from the tomograms is caused by an individual difference or a disease upon giving a diagnosis with reference to the tomograms.

Further features of the present invention will become apparent from the following description of exemplary embodiments (with reference to the attached drawings).

BRIEF DESCRIPTION OF DRAWINGS

FIGS. 8A, 8B, and 8C are views showing difference information display examples at structurally symmetric positions according to the second embodiment;

DESCRIPTION OF EMBODIMENTS

First Embodiment

The arrangement of an image processing apparatus according to this embodiment will be described below with reference to FIG. 1. An image processing apparatus 10 sets a reference tomographic plane indicating a tomographic plane serving as a reference of a tomogram group including a plurality of tomograms obtained by imaging those of an eye to be examined, and generates, for example, parallel tomograms having a predetermined positional relationship based on the reference tomographic plane. The apparatus selects a tomogram at a position designated by an operator, and a tomogram at a position structurally symmetric to the designated position in that eye. Then, the image processing apparatus displays these tomograms to be juxtaposed, thereby executing image processing for assisting a process for judging whether information obtained from the tomograms is caused by an individual difference or disease.

Note that this embodiment will explain a case in which tomograms of three-dimensional data are to be acquired. However, the present invention is not limited to this as long as data which can construct those at positions symmetrical about a line that couples an optic nerve papillary area and a macular region can be acquired. Also, a data acquisition method is not particularly limited as long as data at plane-symmetric positions can be reconstructed by, e.g., interpolation processing from the acquired data.

Figure 1:
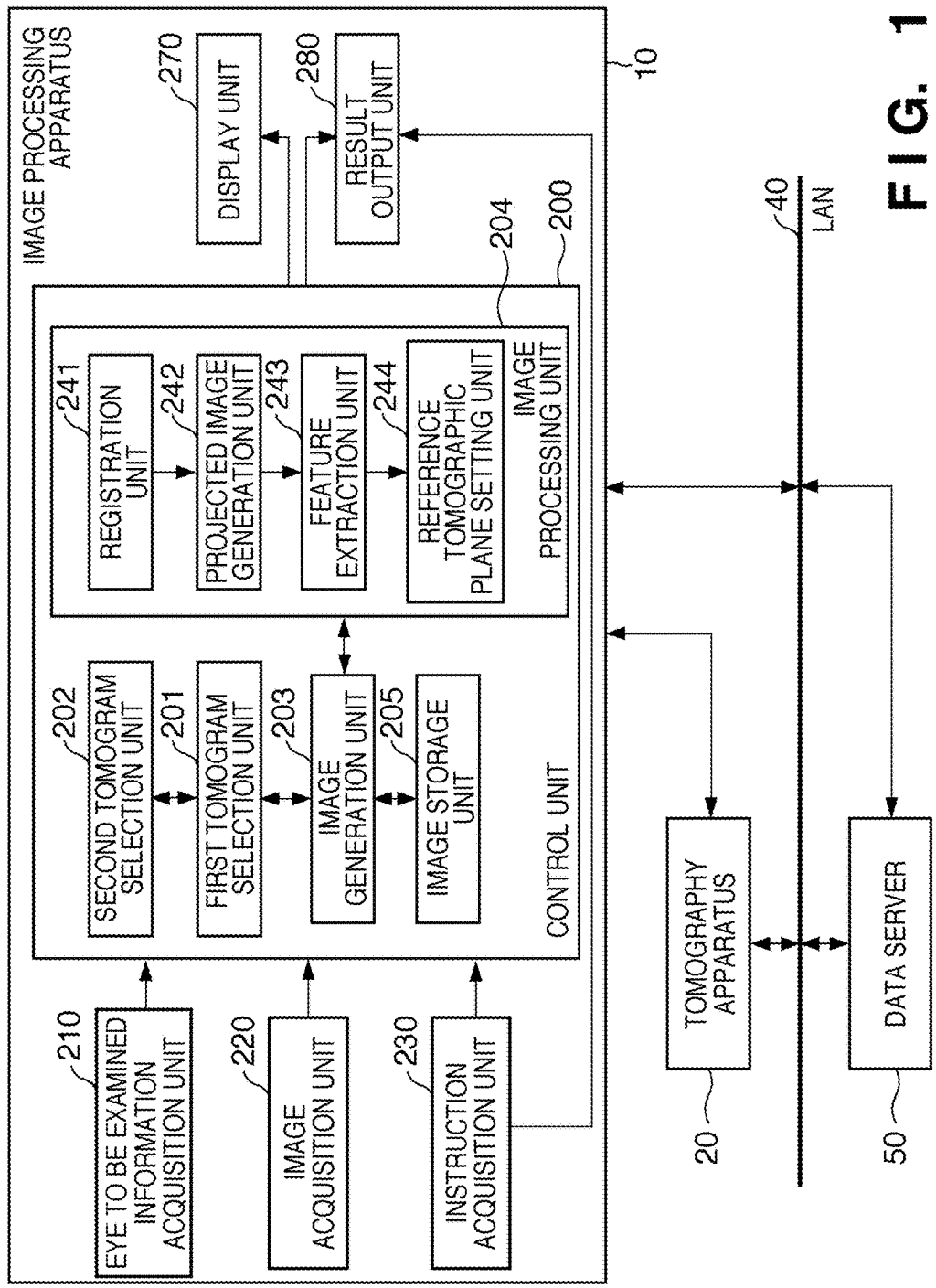
FIG. 1 is a block diagram showing the functional arrangement of an image processing system according to the first embodiment.

The image processing apparatus 10 shown in FIG. 1 is connected to a tomography apparatus 20 via an interface such as USB or IEEE1394, and is connected to a data server 50 via a local area network (LAN) 40. Note that the image processing apparatus 10 may be connected to these apparatuses via an external network such as the Internet.

The tomography apparatus 20 captures tomograms of an eye portion, and includes, for example, a time domain OCT or Fourier domain OCT. The data server 50 is an information processing apparatus (server) which holds tomograms, image feature amounts, and the like of an eye to be examined. The data server 50 saves tomograms of an eye to be examined output from the tomography apparatus 20 and analysis results output from the image processing apparatus 10. Also, the data server 50 transmits previous data associated with an eye to be examined to the image processing apparatus 10 in response to a request from the image processing apparatus 10.

The image processing apparatus 10 includes a control unit 200, eye to be examined information acquisition unit 210, image acquisition unit 220, instruction acquisition unit 230, display unit 270, and result output unit 280. The control unit 200 includes a first tomogram selection unit 201, second tomogram selection unit 202, image generation unit 203, image processing unit 204, and image storage unit 205. The image processing unit 204 includes a registration unit 241, projected image generation unit 242, feature extraction unit 243, and reference tomographic plane setting unit 244, and sets a reference tomographic plane for a tomogram group (volume data). The control unit 200 generates a plurality of tomograms based on this reference tomographic plane.

The eye to be examined information acquisition unit 210 externally acquires information required to discriminate and identify an eye to be examined. The image acquisition unit 220 acquires tomograms transmitted from the tomography apparatus 20. The instruction acquisition unit 230 acquires processing instructions input by the operator. The display unit 270 displays tomograms processed by the control unit 200 on a monitor. The result output unit 280 associates a date and time of examination, the information required to discriminate and identify the eye to be examined, the tomograms of the eye to be examined, and an analysis result obtained by the image processing unit 220 with each other as information to be saved, and transmits that information to the data server 50.

Figure 2A:
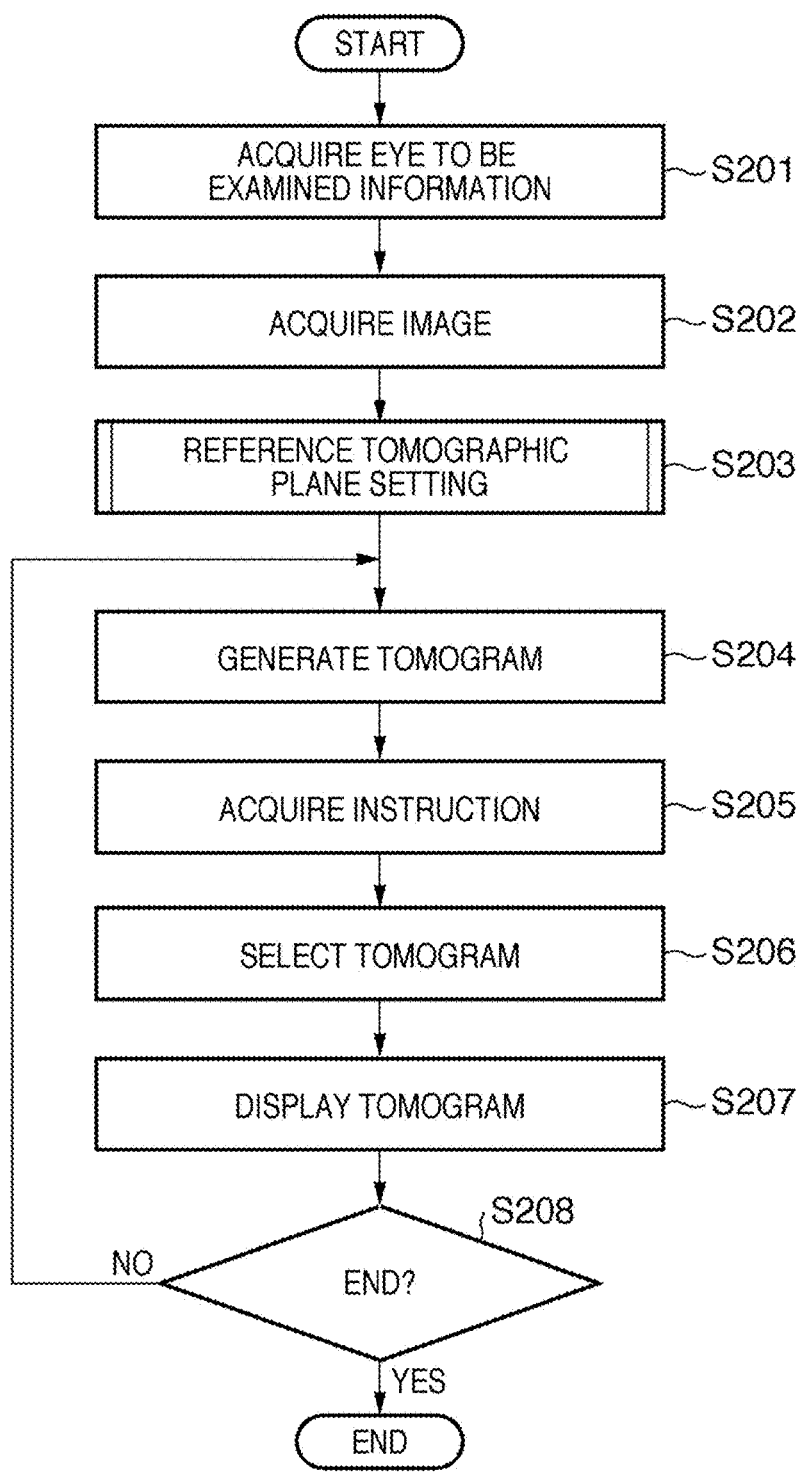
FIGS. 2A and 2B are flowcharts showing the processing sequence of an image processing apparatus according to the first embodiment.

The processing sequence of the image processing apparatus 10 of this embodiment will be described below with reference to the flowchart shown in FIG. 2A. The processes of the flowchart are implemented by executing a program stored in an internal memory (not shown) of the image processing apparatus 10. The processing sequence of this embodiment acquires tomograms of an eye to be examined, and generates a projected image from the tomograms so as to display a broad fundus region. The sequence sets a reference tomographic plane for the tomograms. Then, the sequence selects a plane-symmetric tomogram based on a tomogram at a position which is designated by the operator on the projected image, and the reference tomographic plane, and displays the selected tomograms.

In step S201, the eye to be examined information acquisition unit 210 externally acquires an object identification number as information required to discriminate and identify an eye to be examined. Then, the unit 210 acquires information (a name, age, gender, and the like of a patient) associated with the eye to be examined, which is held by the data server 50, based on the object identification number.

In step S202, the image acquisition unit 220 acquires tomograms transmitted from the tomography apparatus 20. The acquired tomograms configure a tomogram group. Then, the unit 220 transmits the acquired information to the image storage unit 205. The following description will be made under the condition that the tomograms acquired by the image acquisition unit 220 are those of the eye to be examined identified by the eye to be examined information acquisition unit 210.

In step S203, the image processing unit 204 sets a reference tomographic plane indicating a tomographic plane serving as a reference for tomograms. The process of this step will be described in detail later using the flowchart shown in FIG. 2B.

Figure 4A:
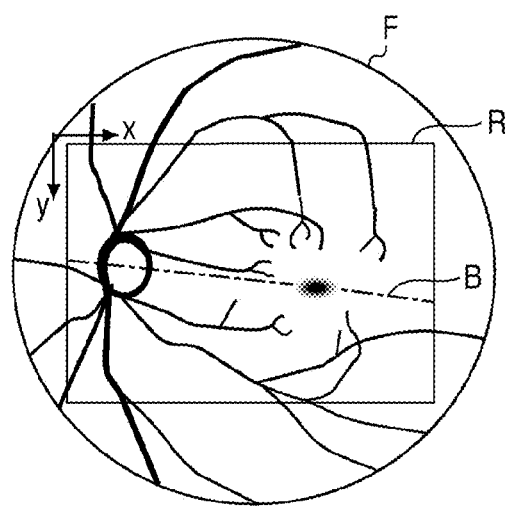
FIGS. 4A, 4B, and 4C are views for explaining tomogram positions according to the first embodiment.

In step S204, the image generation unit 203 generates tomograms from the tomogram group (volume data). In this step, the unit 203 generates the reference tomographic plane and a plurality of tomograms parallel to the reference tomographic plane. The generation process of the reference tomographic plane and tomograms will be described below with reference to FIG. 4A. Referring to FIG. 4A, reference symbol F denotes an eye fundus; R, a rectangular region where a tomogram is obtained in the eye fundus F; and B, a one-dashed chain line indicating the position of the reference tomographic plane.

Figure 4B:
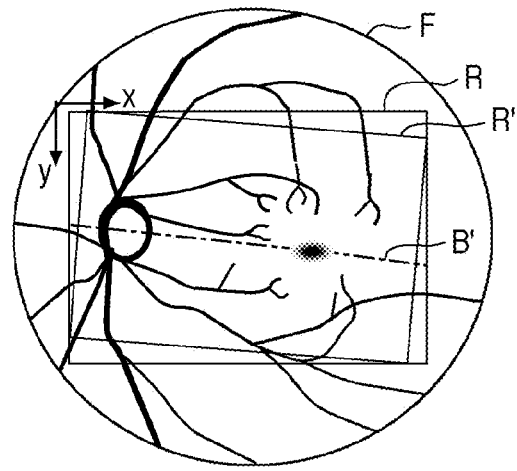

Upon generating tomograms from the tomogram group, pixels which are located at coordinates that are not acquired upon image capturing are generated by image interpolation. As a method of image interpolation, for example, a bicubic method is used to generate tomograms. Note that the reference tomographic plane is set in the rectangular region R in FIG. 4A. However, the present invention is not limited to such specific example. For example, as shown in FIG. 4B, a rectangular region R' parallel to the reference tomographic plane may be set, and tomograms may be generated from the tomogram group within the rectangular region R'.

In step S205, the instruction acquisition unit 230 acquires a position designated by the operator on a projected image or the tomogram group. However, if no operator's instruction is acquired, the reference tomographic plane set in step S203 is used as the designated position. As a method of designating a position of interest by the operator, he or she may directly designate a point using, e.g., a mouse, or may designate the position of interest by operating a slider or a mouse wheel, or by inputting a distance from the reference tomographic plane as a numerical value.

In step S206, the first and second tomogram selection units 201 and 202 respectively select tomograms to be displayed on the display unit 270 based on the reference tomographic plane and the position acquired by the instruction acquisition unit 230. The tomogram selection process will be described below with reference to FIG. 4C.

Figure 4C:
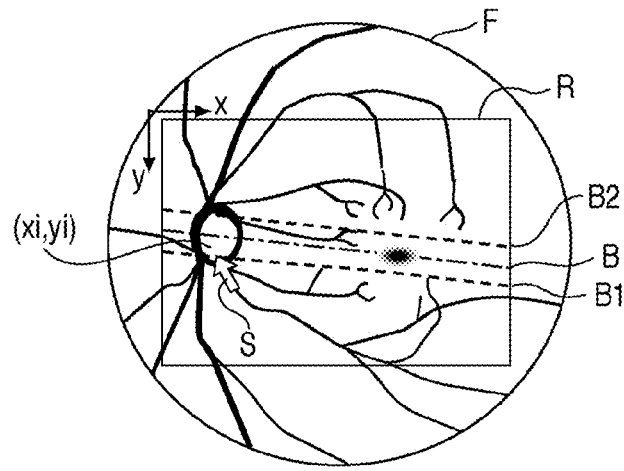

In FIG. 4C, an arrow S indicates a position $(x_i, y_j)$ designated by the operator. A broken line B1 represents a tomogram position selected by the first tomogram selection unit 201, and a broken line B2 represents that selected by the second tomogram selection unit 202.

The first tomogram selection unit 201 selects a tomogram corresponding to the designated position acquired in step S205 from the plurality of tomograms generated in step S204. The second tomogram selection unit 202 selects a tomogram at a position which is plane-symmetric to the two-dimensional tomogram selected by the first tomogram selection unit 201 with respect to the reference tomographic plane from the plurality of tomograms generated in step S204.

Figure 5:
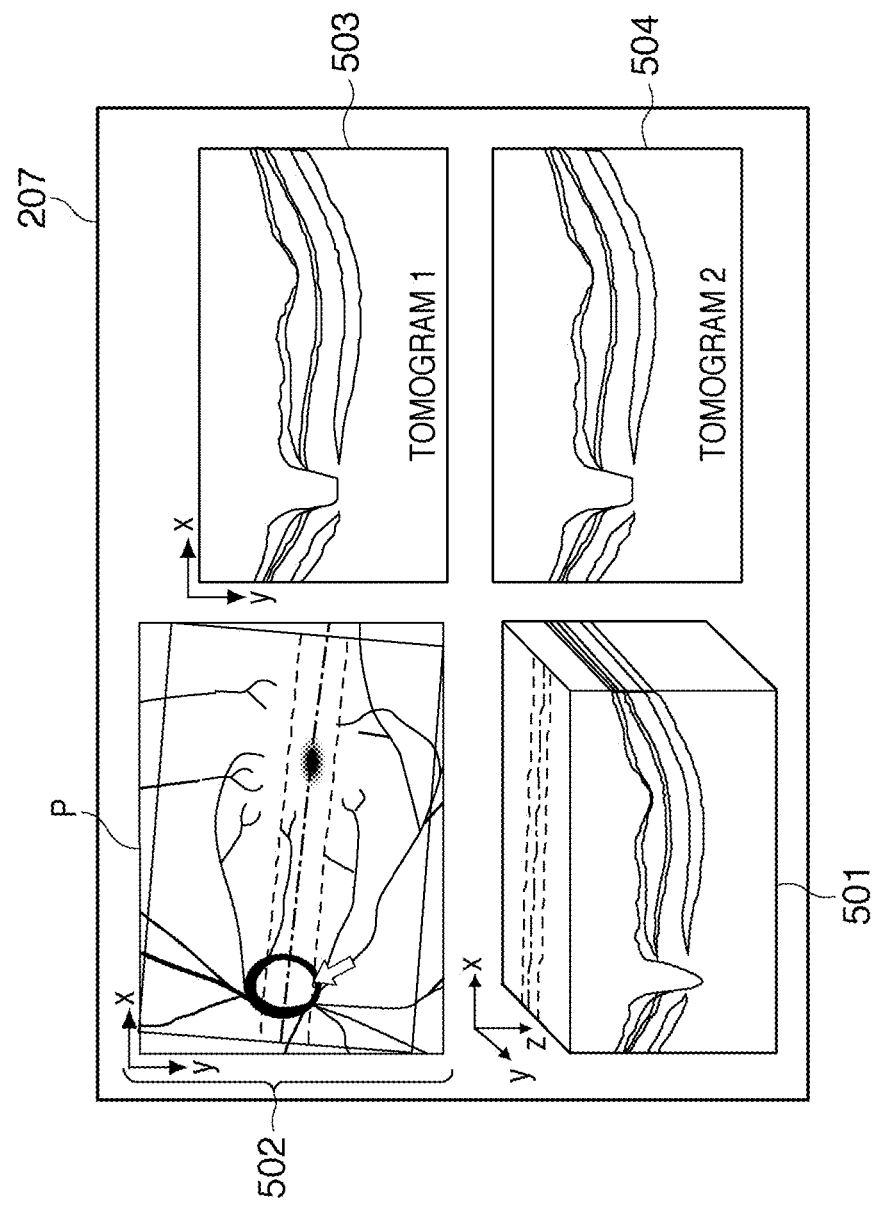
FIG. 5 is a view showing a display example of tomograms according to the first embodiment.

In step S207, the tomograms selected in step S206 are displayed on the display unit 270. FIG. 5 shows a screen display example. In FIG. 5, a three-dimensional tomogram group 501, projected image 502, tomogram 1 503 at the position designated by the operator, and tomogram 2 504 located at a plane-symmetric position based on the reference tomographic plane are displayed on the display unit 270. The tomogram 1 503 and tomogram 2 504 are displayed to be juxtaposed at upper and lower positions. The positions of the tomogram 1 503 and tomogram 2 504 generated from the tomogram group are respectively displayed on the projected image 502. Upon displaying the positions of the tomograms on the projected image, the position of the reference tomographic plane is also displayed, and different colors and line types of position information can be used. For example, assume that a color of a line which represents the position of the tomogram 1 503 is red, and that of a line which represents the position of the tomogram 2 504 is blue. Note that color settings, line types, ON/OFF of position display on the projected image, and the like can be changed using a user interface (not shown).

When the position of the tomogram 1 503 is changed, the second tomogram selection unit 202 displays the tomogram 2 504 at a position corresponding to the changed tomogram 1 503. As a display method, when the position of the tomogram 1 503 is continuously changed using, e.g., a slider or mouse, the position of the tomogram 2 504 is also synchronously and continuously changed and displayed. Alternatively, while the position of the tomogram 1 503 is continuously changed, the position of the tomogram 2 504 is left unchanged, and when the position of the tomogram 1 503 is settled, a tomogram at a position plane-symmetric to the tomogram 1 503 may be selected and displayed.

In step S208, the instruction acquisition unit 230 externally acquires an instruction as to whether or not to end the tomogram analysis processing by the image processing apparatus 10. This instruction is input by the operator using a user interface (not shown). If the operator designates a position of interest for the tomogram group or two-dimensional tomogram without ending the processing, the process returns to step S204. If the instruction to end the processing is acquired, the image processing apparatus 10 ends its processing.

Figure 2B:
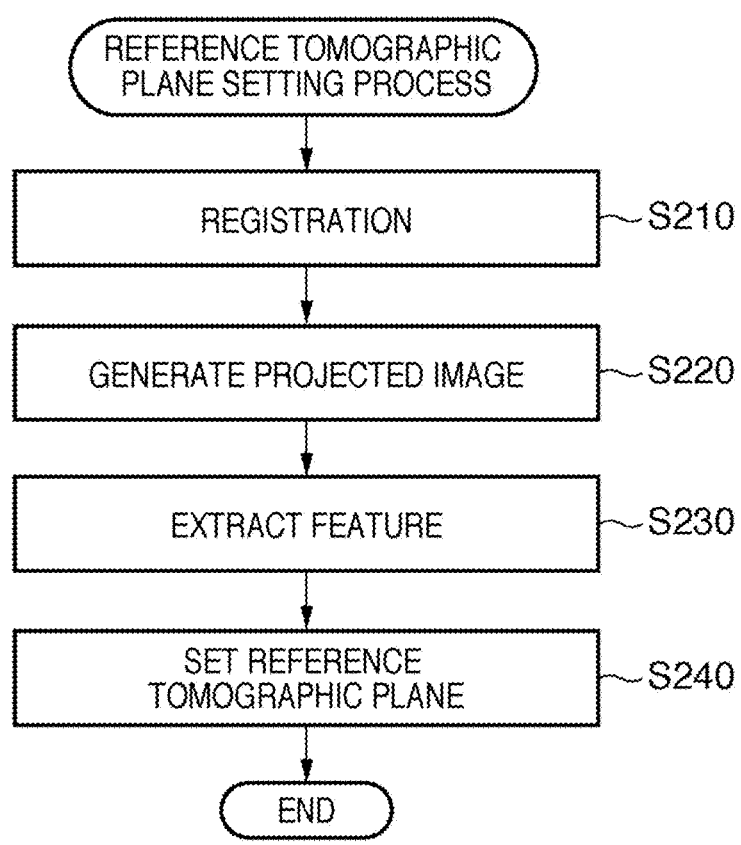

The reference tomographic plane setting process in step S203 will be described below with reference to FIG. 2B.

In step S210, the registration unit 241 registers the positions among tomograms $T_1$ to $T_n$. The unit 241 defines an evaluation function that represents a similarity between two tomograms in advance, and deforms images to obtain the best value of the evaluation function. As the evaluation function, a method of evaluating a similarity using pixel values can be used. For example, evaluation is made using mutual information contents. Upon deforming an image, affine transformation can be used to attain translation and rotation and to change an enlargement factor.

Figure 3A:
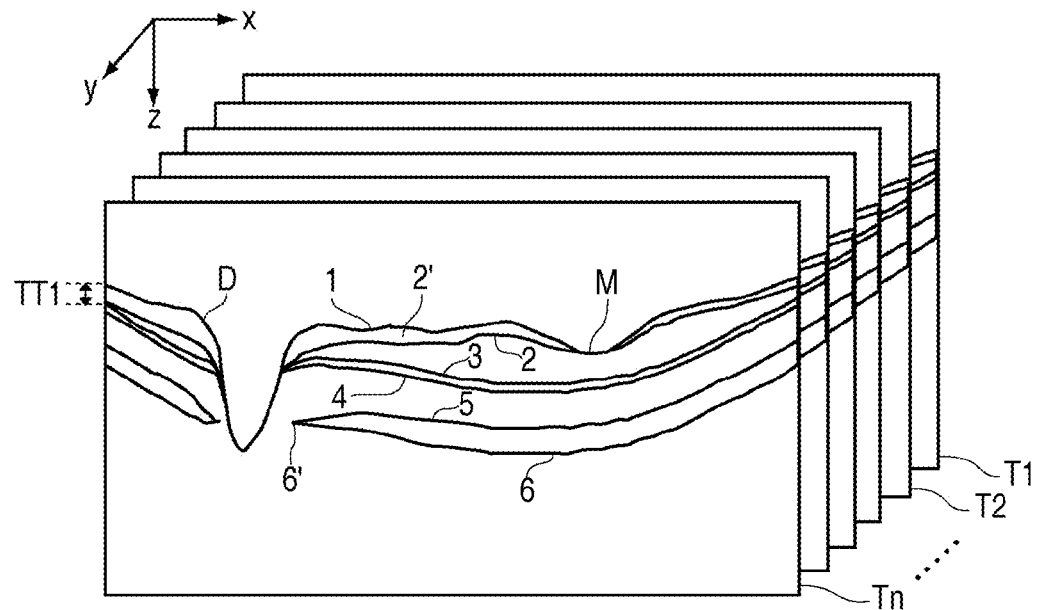
FIGS. 3A and 3B are views showing an example of tomograms and a projected image according to the first embodiment.
Figure 3B:
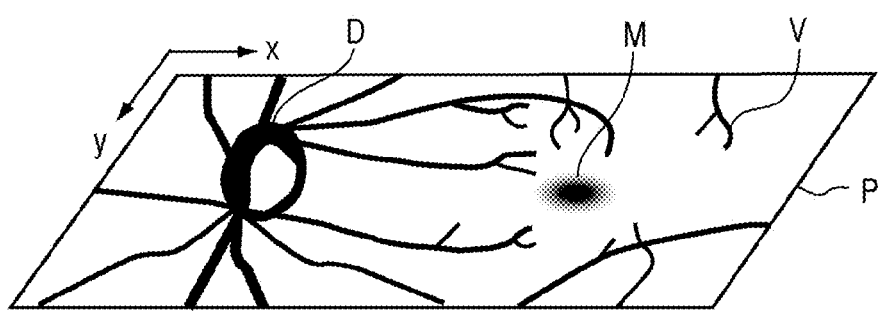

In step S220, the projected image generation unit 242 generates a projected image by integrating respective tomograms in a depth direction. FIGS. 3A and 3B show examples of tomograms of retina layers and a projected image. FIG. 3A shows tomograms of retina layers, and FIG. 3B shows a projected image P generated by integrating luminance values of the tomograms in the depth direction (z-direction). In the projected image P, a curve v represents a blood vessel, D represents an optic nerve papillary area, and M represents a macular region.

In step S230, the feature extraction unit 243 extracts the centers of the optic nerve papillary area D and macular region M from the tomograms.

An example of the method of extracting the center of the optic nerve papillary area D will be described below. In order to detect a region of the optic nerve papillary area D, the retinal pigment epithelial layer edge 6' is detected in the tomogram group shown in FIG. 3A. The retinal pigment epithelial layer boundary 6 is a high-luminance region, and can be detected using feature amounts of a filter which emphasizes layer structures or that which emphasizes edges. Then, the retinal pigment epithelial layer edge 6' near an optic nerve papilla fovea is detected from the retinal pigment epithelial layer boundary 6. Then, the detected retinal pigment epithelial layer edges 6' are coupled in a three-dimensional region to form an optic nerve papillary region. The optic nerve papillary region undergoes outlier removal or morphology processing to define the optic nerve papillary area D. As the center of the optic nerve papillary area D, a barycentric position of the region is used.

An example of the method of extracting a central fovea of the center of the macular region M will be described below. In order to detect the central fovea, the inner limiting membrane 1 is detected in the tomogram group shown in FIG. 3A. The inner limiting membrane 1 is also detected using layer or edge features as in the retinal pigment epithelial layer boundary 6. Since the central fovea has a recessed shape in a retina, it is extracted using shape features of the detected inner limiting membrane 1. In the macular region M, since points having large curvatures are concentrated, the curvatures are calculated at respective points of the detected inner limiting membrane 1, and an overall region where the points with the large curvatures are concentrated is extracted. In the extracted region, a portion which is located at a deepest portion in the three-dimensional tomogram is detected as the central fovea.

In step S240, the reference tomographic plane setting unit 244 sets a plane including a line that couples the centers of the optic nerve papillary area D and macular region M extracted by the feature extraction unit 243 as the reference tomographic plane.

In a three-dimensional space, a plane can be calculated from arbitrary three points on the space and an equation of plane $ax+by+cz+d=0$. Therefore, the reference tomographic plane can be set based on two arbitrary different points located on the line that couples the centers of the optic nerve papillary area D and macular region M, and one point located at a position perpendicular to these points in the z-direction.

In the reference tomographic plane setting process, the process for automatically setting the reference tomographic plane has been described. However, the reference tomographic plane need not always be automatically set, but it may be set at a position designated by the operator. For example, the operator may set the central positions of the optic nerve papillary area and macular region, or may modify the reference tomographic plane set by the computer.

This embodiment has explained the processing for setting the reference tomographic plane in the retina of the eye to be examined in advance, generating tomograms parallel to the reference tomographic plane, and then designating a tomogram. However, the present invention is not limited to this. For example, the following processing may be executed. A plurality of tomograms at arbitrary positions and in arbitrary directions are generated in advance from a tomogram group (volume data) of a retina, which is captured in advance. A tomogram corresponding to a position designated by the operator is selected from the generated tomograms. A tomogram which is located at a position symmetric to the designated tomogram with respect to the reference tomographic plane is generated from the tomogram group of the retina, which is captured in advance, and the designated tomogram and the generated tomogram may be displayed to be juxtaposed.

According to the aforementioned arrangement, a tomogram at a position designated by the operator is selected, a tomogram at a position structurally symmetric to the designated position is selected, and these tomograms are displayed to be juxtaposed. Then, when the operator gives a diagnosis with reference to the tomograms, he or she can easily judge whether information obtained from the tomograms is caused by an individual difference or disease.

Second Embodiment

The second embodiment will explain an arrangement when a measurement unit 245 is added to the arrangement of the first embodiment and some operations of the feature extraction unit 243 are changed. Unlike in the first embodiment, a feature extraction unit 2431 extracts boundaries of respective layers from retina layers, the measurement unit 245 measures layer thickness differences between a tomogram 1 and a tomogram 2 which is structurally symmetric to the tomogram 1, and a display unit 270 displays difference information indicating the difference measurement results.

Figure 6:
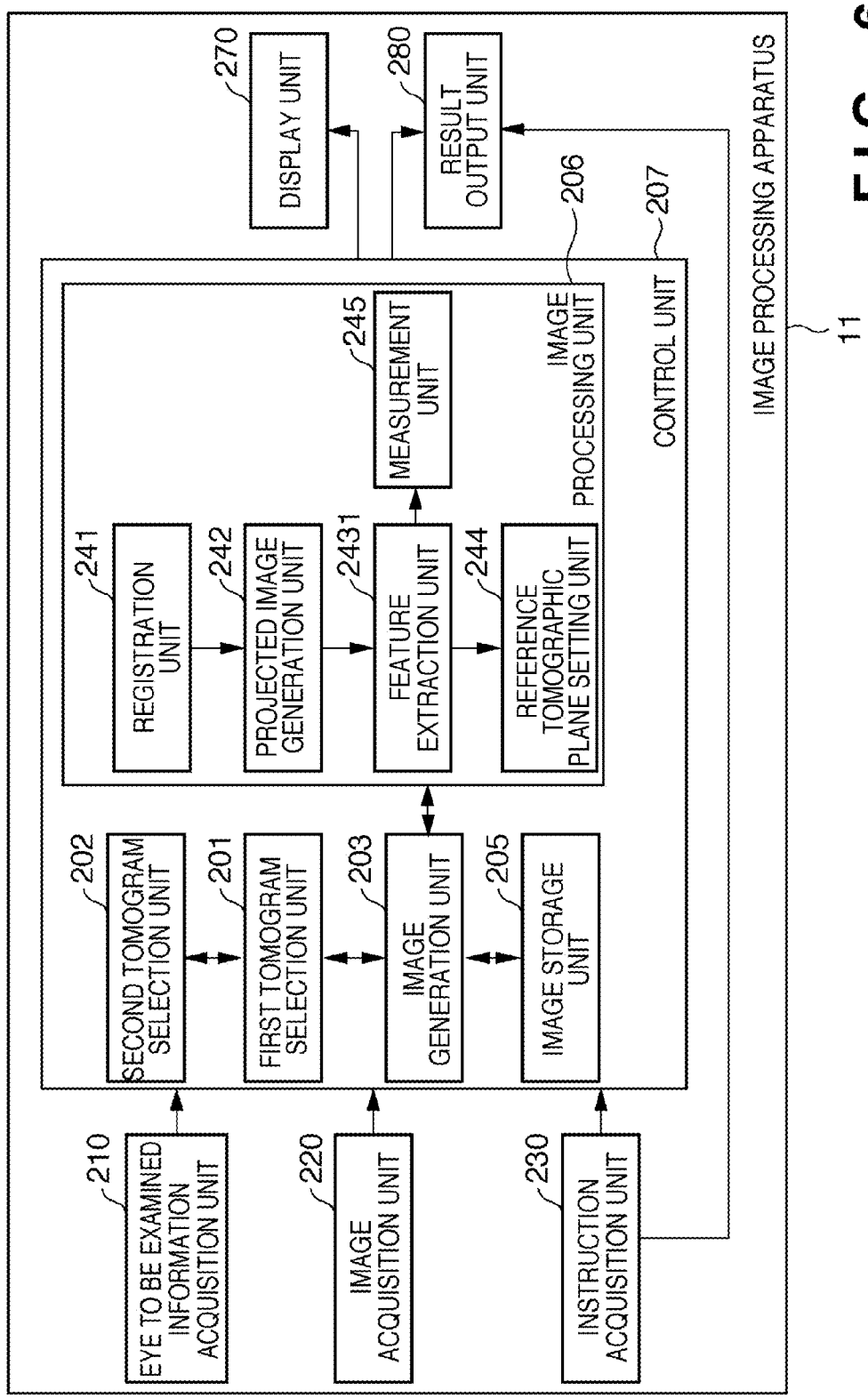
FIG. 6 is a block diagram showing the functional arrangement of an image processing apparatus according to the second embodiment.

FIG. 6 is a block diagram showing the functional arrangement of an image processing apparatus 11 of this embodiment. An image processing unit 206 shown in FIG. 6 includes a registration unit 241, a projected image generation unit 242, the feature extraction unit 2431, a reference tomographic plane setting unit 244, and the measurement unit 245. Since the operations of the registration unit 241, projected image generation unit 242, and reference tomographic plane setting unit 244 are the same as those in the first embodiment, a description thereof will not be repeated.

The processing sequence of the image processing apparatus 11 of this embodiment will be described below with reference to the flowcharts shown in FIGS. 7A and 7B. The processes of these flowcharts are implemented by executing a program stored in an internal memory (not shown) of the image processing apparatus 11. Note that steps other than steps S730, S707, and S708 are the same as those in the first embodiment, and a description thereof will not be repeated.

Figure 7A:
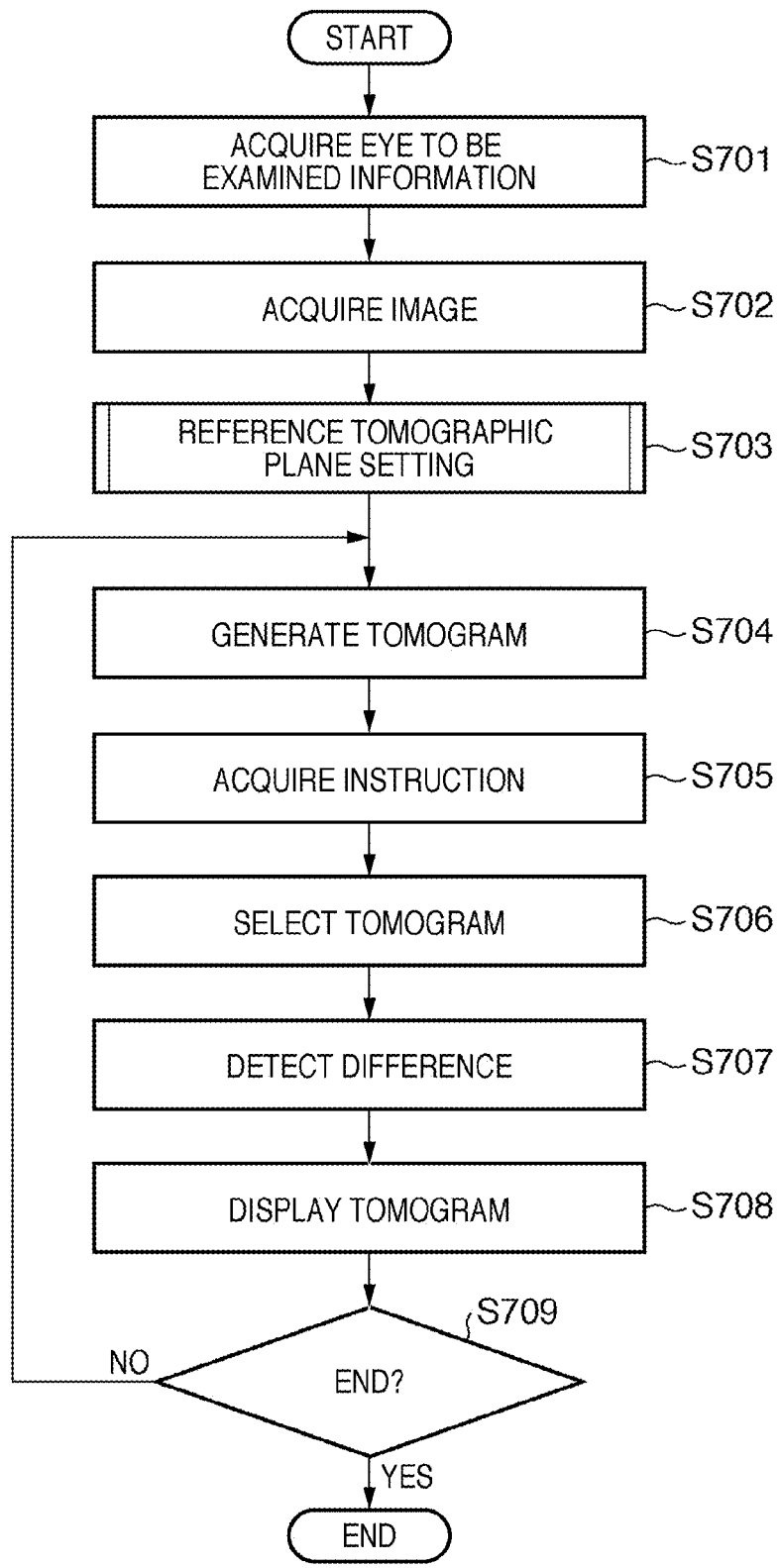
FIGS. 7A and 7B are flowcharts showing the processing sequence of the image processing apparatus according to the second embodiment.

In step S707 in FIG. 7A, the measurement unit 245 measures the thicknesses of respective layers based on the layer boundaries detected in step S730. Then, the unit 245 measures differences between the layer thicknesses of tomograms 1 and 2. Alternatively, the unit 245 may measure differences between data in a standard database registered in a data server 50 and the thicknesses of respective layers.

In step S708, the display unit 270 displays difference information of the layer thicknesses (the distribution of layer structures) calculated in step S707 together with a tomogram selected in step S706. FIGS. 8A, 8B, and 8C show measurement examples of differences between nerve fiber layers 2' in the tomograms 1 and 2, that is, display examples of differences between layer thicknesses.

Figure 7B:
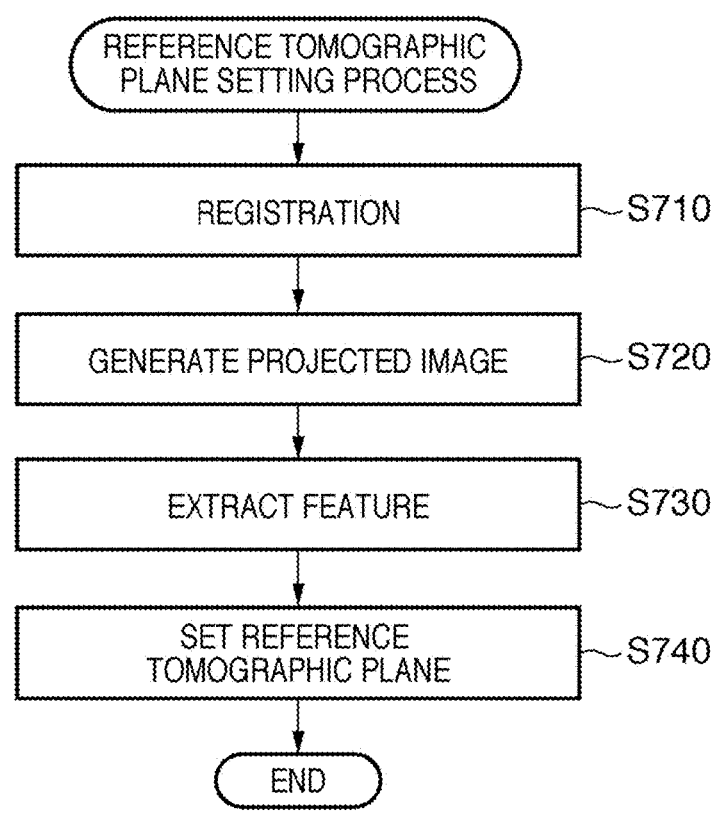

In a reference tomographic plane setting process, in step S730 in FIG. 7B, the feature extraction unit 2431 extracts the centers of an optic nerve papillary area D and macular region M, and extracts respective layers from retina layers. In the same manner as in step S230 of the first embodiment in which an inner limiting membrane 1 and retinal pigment epithelial layer boundary 6 are detected, the feature extraction unit 2431 detects a nerve fiber layer boundary 2, inner plexiform layer boundary 3, outer plexiform layer boundary 4, and junction 5 between inner and outer photoreceptor segments in this step.

Not all of the boundaries of the illustrated respective layers need be detected, and an operator may select types of layers to be detected via a user interface (not shown), or types of layers to be detected may be selected according to the type of an eye disease or a degree of disease.

FIG. 8A shows an example in which the thickness difference information is superimposed on the nerve fiber layer 2' of the tomogram 2. Diff1 represents a portion where the nerve fiber layer 2' of the tomogram 2 becomes thicker than the tomogram 1, and Diff2 represents a portion where the nerve fiber layer 2' of the tomogram 2 becomes thinner than the tomogram 1. Depending whether the layer displayed in the tomogram 2 becomes thicker or thinner than that displayed in the tomogram 1, they may be displayed using different colors, pattern types, or densities. FIG. 8B shows an example in which a tomogram 1 801, tomogram 2 802, and thickness difference graph 803 are displayed to be juxtaposed. The thickness difference graph expresses whether the layer thickness displayed in the tomogram 2 is thicker or thinner with reference to the tomogram 1. FIG. 8C shows an example in which difference information between a lower region R1' and upper region R2' divided to have a reference tomographic plane B as a boundary is superimposed on a projected image. FIG. 8C shows an example in which a rectangular region R' is divided into some small regions, and difference information between thicknesses in these regions is displayed. A maximum value, average value, median, minimum value, and the like of differences in the rectangular region may be displayed as numerical values, or may be displayed using colors. For example, the operator may be allowed to judge thickness changes based on colors: a portion with no thickness change may be displayed in green, a thinner portion may be displayed in blue, and so forth. When differences are displayed using colors, they may be displayed for respective pixels using different colors in addition to divided small regions.

Figure 9A:
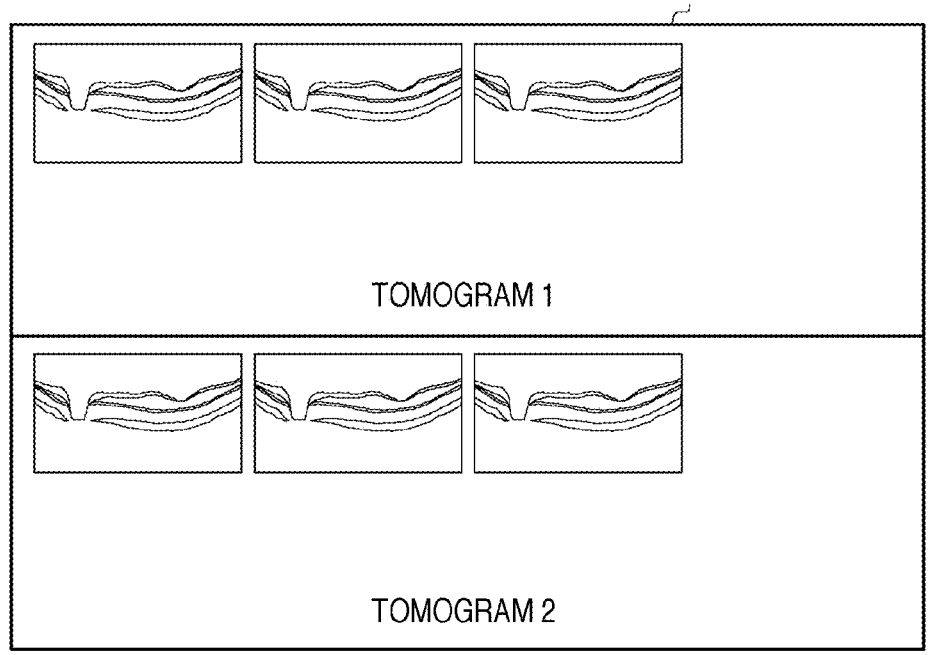
FIGS. 9A and 9B are views showing tomogram display examples in which differences are detected according to the second embodiment.
Figure 9B:
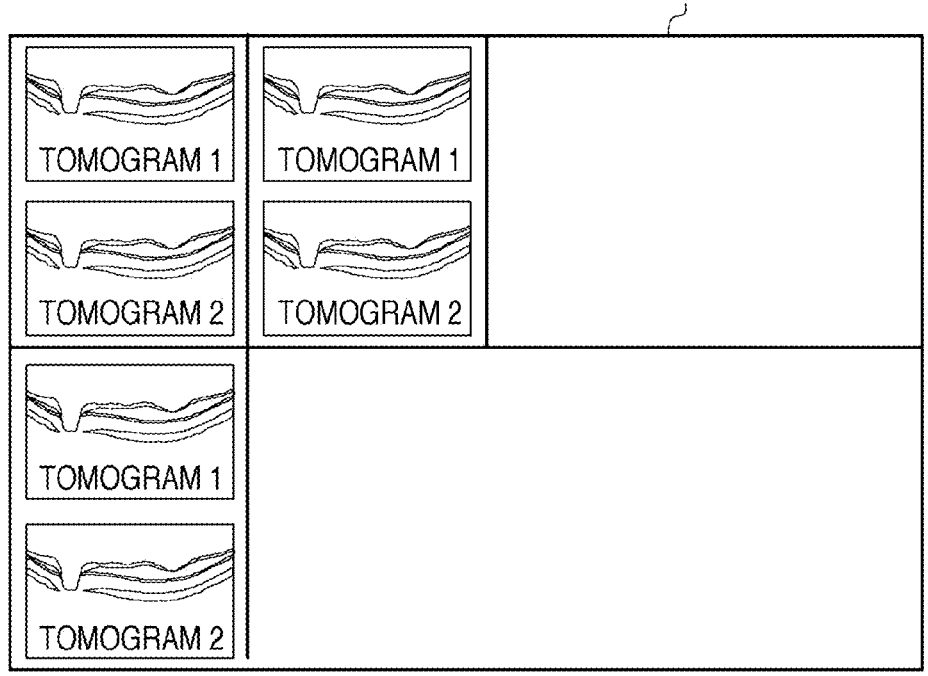

FIGS. 9A and 9B show image display examples of tomograms when differences are detected between the tomograms 1 and 2. FIG. 9A shows an example in which portions where large differences are detected are displayed as a list, that is, display regions of the tomograms 1 and 2 are separately displayed as a list. FIG. 9B shows a comparison display example of portions where large differences are detected, that is, the tomograms 1 and 2 are displayed to be juxtaposed. The screens shown in FIGS. 9A and 9B and that shown in FIG. 5 may be displayed selectively or simultaneously using independent windows.

According to the aforementioned arrangement, together with a tomogram at a position designated by the operator, a tomogram at a position structurally symmetric to the designated position in the same eye is displayed to be juxtaposed, and difference information of layer thicknesses between the displayed tomograms is also displayed. Since the differences between the layer thicknesses of the structurally symmetric portions are displayed using numerical values, colors, or a graph, the operator can easily make a judgment upon giving a diagnosis with reference to the tomograms.

Third Embodiment

In this embodiment, a control unit 208 includes a first image generation unit 211 and second image generation unit 212, and does not include the first tomogram selection unit 201 and second tomogram selection unit 202 unlike in the control unit 207 of the second embodiment. In this embodiment, a tomogram at an arbitrary position and in an arbitrary direction designated by an operator is generated in real time from a tomogram group (volume data) of a retina of an eye to be examined, which is captured in advance. Then, a tomogram which is plane-symmetric to that tomogram with respect to a reference tomographic plane is generated, and these tomograms are displayed to be juxtaposed. In this case, since images need not be generated in advance, a memory size required to store images can be reduced, and the processing time required until a first tomogram is displayed can be shortened.

Figure 10:
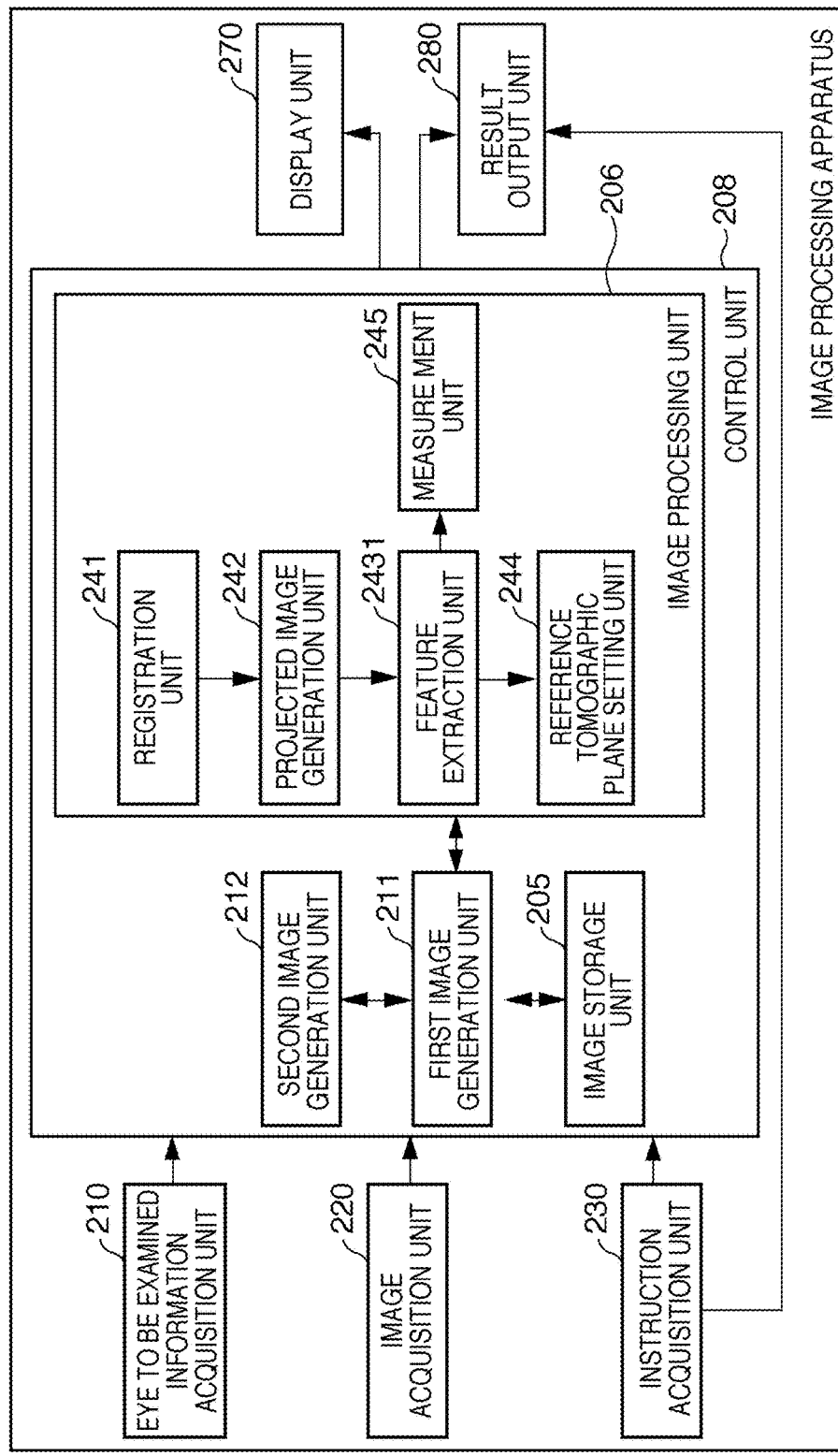
FIG. 10 is a block diagram showing the functional arrangement of an image processing apparatus according to the third embodiment.

FIG. 10 is a block diagram showing the functional arrangement of an image processing apparatus 12 of this embodiment. Since the arrangement other than the first and second image generation units 211 and 212 in FIG. 10 is the same as that of the second embodiment, a description thereof will not be repeated.

The first image generation unit 211 generates, in real time, a tomogram at a position and in a direction designated by the operator from a tomogram group (volume data) of a retina, which is captured in advance. The second image generation unit 212 generates a tomogram which has a plane symmetry relationship with the tomogram generated by the first image generation unit 211 with respect to the reference tomographic plane. A display unit 270 displays the tomograms generated by the first and second image generation units 211 and 212 to be juxtaposed.

According to the arrangement of this embodiment, a tomogram at a position designated by the operator is acquired, a tomogram at a position structurally plane-symmetric to the designated position is acquired, and these tomograms are displayed to be juxtaposed. Then, when the operator gives a diagnosis with reference to the tomograms, he or she can easily judge whether information obtained from the tomograms is caused by an individual difference or disease.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-166181, filed Jul. 14, 2009, which is hereby incorporated by reference herein in its entirety.

The invention claimed is:

1. A processing apparatus for use in tomography, the processing apparatus comprising:
   a processor-implemented comparison unit configured to compare, based on volume data including a plurality of tomograms obtained using optical coherence tomography, values regarding layer thicknesses at symmetrical positions with respect to a line that couples, in a fundus, a macular region and an optic nerve papillary region; and
   a display control unit configured to cause a display unit to display, on a two-dimensional image indicating two-dimensional positional relations of the symmetrical positions, information indicating a comparison result produced by the comparison unit,
   wherein the comparison unit automatically obtains, as the comparison result, a difference between the values regarding layer thicknesses at symmetrical positions with respect to the line that couples the macular region and the optic nerve papillary region,
   wherein the display control unit causes the display unit to change the display form in accordance with the difference between the values regarding layer thicknesses at the symmetrical positions with respect to the line that couples the macular region and the optic nerve papillary region, and
   wherein the display form includes a display color.

2. The apparatus according to claim 1, wherein the comparison unit is configured to compare layer thicknesses in small regions located at symmetrical positions with respect to the line that couples the macular region and the optic nerve papillary region, and
   wherein the small regions are defined by (i) the line that couples the macular region and the optic nerve papillary region, and (ii) a plurality of lines parallel to the line that couples the macular region and the optic nerve papillary region, and (iii) a plurality of lines perpendicular to the line that couples the macular region and the optic nerve papillary region.

3. The apparatus according to claim 2, wherein, for each small region, the layer thickness is an average value of layer thicknesses obtained from the small region.

4. The apparatus according to claim 3, wherein the display control unit causes the display unit to display (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region, and
   wherein the display control unit causes the display unit to display information indicating the comparison result corresponding to each small region.

5. The apparatus according to claim 4, wherein the display control unit causes the display unit to display the information indicating the comparison result corresponding to each small region, at a position corresponding to the small region.

6. The apparatus according to claim 2, wherein the display control unit causes the display unit to display an image showing a surface of the fundus and (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region by superimposing (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region, on the image showing the surface of the fundus.

7. The apparatus according to claim 2, wherein the display control unit causes the display unit to display (i) the line that couples the macular region and the optic nerve papillary region, and (ii) the plurality of lines parallel to the line that couples the macular region and the optic nerve papillary region, and (iii) the plurality of lines perpendicular to the line that couples the macular region and the optic nerve papillary region, and wherein the display control unit causes the display unit to display information indicating the comparison result corresponding to each small region.

8. The apparatus according to claim 7, wherein the display control unit causes the display unit to display the information indicating the comparison result corresponding to each small region, at a position corresponding to the small region.

9. The apparatus according to claim 7, wherein the line that couples, in the fundus, the macular region and the optic nerve papillary region, is a line that couples, in the fundus, a center of the macular region and a center of the optic nerve papillary region.

10. The apparatus according to claim 2, wherein the display control unit causes the display unit to display an image showing a surface of the fundus and (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region by superimposing (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region, on the image showing a surface of the fundus, and wherein the display control unit causes the display unit to display the information indicating the comparison result corresponding to each small region by superimposing the information indicating the comparison result corresponding to each small region on the image showing the surface of the fundus.

11. The apparatus according to claim 1, wherein the line that couples, in the fundus, the macular region and the optic nerve papillary region, is a line that couples, in the fundus, a center of the macular region and a center of the optic nerve papillary region.

12. The apparatus according to claim 1, wherein the values regarding layer thicknesses at symmetrical positions include an average value.

13. The apparatus according to claim 12, wherein the line that couples, in the fundus, the macular region and the optic nerve papillary region, is a line that couples, in the fundus, a center of the macular region and a center of the optic nerve papillary region.

14. A processing apparatus for use in tomography, the processing apparatus comprising:

a processor-implemented comparison unit configured to compare, based on a volume data including a plurality of tomograms obtained using optical coherence tomography, values regarding layer thicknesses at symmetrical positions with respect to a line that couples, in a fundus, a macular region and an optic nerve papillary region; and a display control unit configured to cause a display unit to display, on a two-dimensional image indicating two-dimensional positional relations of the symmetrical positions, information indicating a comparison result produced by the comparison unit, wherein the comparison unit automatically compares layer thicknesses in small regions located at symmetrical positions with respect to the line that couples the macular region and the optic nerve papillary region, and wherein the small regions are defined by (i) the line that couples the macular region and the optic nerve papillary region, and (ii) a plurality of lines parallel to the line that couples the macular region and the optic nerve papillary region, and (iii) a plurality of lines perpendicular to the line that couples the macular region and the optic nerve papillary region.

15. The apparatus according to claim 14, wherein, for each small region, the layer thickness is an average value of layer thicknesses obtained from the small region.

16. The apparatus according to claim 14, wherein the display control unit causes the display unit to display an image showing a surface of the fundus and (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region by superimposing (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region, on the image showing the surface of the fundus.

17. The apparatus according to claim 14, wherein the display control unit causes the display unit to display (i) the line that couples the macular region and the optic nerve papillary region, and (ii) the plurality of lines parallel to the line that couples the macular region and the optic nerve papillary region, and (iii) the plurality of lines perpendicular to the line that couples the macular region and the optic nerve papillary region, and wherein the display control unit causes the display unit to display information indicating the comparison result corresponding to each small region.

18. The apparatus according to claim 14, wherein the display control unit causes the display unit to display the information indicating the comparison result corresponding to each small region, at a position corresponding to the small region.

19. The apparatus according to claim 14, wherein the display control unit causes the display unit to display an image showing a surface of the fundus and (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region by superimposing (i) the line that couples the macular region and the optic nerve papillary region, (ii) the plurality of lines parallel to the line that couples the macular region and the optic nerve papillary region, and (iii) the plurality of lines perpendicular to the line that couples the macular region and the optic nerve papillary region, on the image showing the surface of the fundus, and wherein the display control unit causes the display unit to display the information indicating the comparison result corresponding to each small region by superimposing the information indicating the comparison result corresponding to each small region on the image showing the surface of the fundus.

20. The apparatus according to claim 7, wherein the line that couples, in the fundus, the macular region and the optic nerve papillary region, is a line that couples, in the fundus, a center of the macular region and a center of the optic nerve papillary region.

21. The apparatus according to claim 14, wherein the display control unit is configured to change the display form of the information indicating the comparison result in accordance with the comparison result.

22. The apparatus according to claim 14, wherein the values regarding layer thicknesses at symmetrical positions include an average value.

23. A non-transitory computer-readable storage medium storing a computer program which instructs a computer to execute a method of comparing layer thicknesses for use in tomography, the method comprising:

a comparison step of comparing, based on a volume data including a plurality of tomograms obtained using optical coherence tomography, values regarding layer thicknesses at symmetrical positions with respect to a line that couples, in a fundus, a macular region and an optic nerve papillary region, and of automatically obtaining, as a comparison result, a difference between the values regarding layer thicknesses at symmetrical positions with respect to the line that couples the macular region and the optic nerve papillary region; and a display control step of displaying, on a two-dimensional image indicating two-dimensional positional relations of the symmetrical positions, information indicating the comparison result that is the difference between the values regarding layer thicknesses at symmetrical positions with respect to the line that couples the macular region and the optic nerve papillary region, using a display form that is changed in accordance with the comparison result that is the difference between the values regarding layer thicknesses at symmetrical positions with respect to the line that couples the macular region and the optic nerve papillary region.

24. The non-transitory computer-readable storage medium according to claim 23, further comprising a determination step of determining automatically the symmetrical positions with respect to the line that couples, in the fundus, the macular region and the optic nerve papillary region.

25. The non-transitory computer-readable storage medium according to claim 23, wherein the values regarding layer thicknesses at symmetrical positions include an average value.

26. A processing apparatus for use in tomography, the processing apparatus comprising:

a processor-implemented comparison unit configured to compare, based on a volume data including a plurality of tomograms obtained using optical coherence tomography, values regarding layer thicknesses at symmetrical positions with respect to a line that couples, in a fundus, a macular region and an optic nerve papillary region; and a display control unit configured to cause a display unit to display, on a two-dimensional image indicating two-dimensional positional relations of the symmetrical positions, information indicating a comparison result by the comparison unit, wherein the comparison unit automatically obtains, as the comparison result, a difference between the values regarding layer thicknesses at symmetrical positions with respect to the line that couples the macular region and the optic nerve papillary region, and wherein the display control unit causes the display unit to display as the information indicating a comparison result, using a display form in accordance with the difference between the values regarding layer thicknesses at symmetrical positions with respect to the line that couples the macular region and the optic nerve papillary region, information indicating the difference between the values regarding layer thicknesses at symmetrical positions with respect to the line that couples the macular region and the optic nerve papillary region.

27. A processing system for use in tomography, the system comprising:

an optical coherence tomography apparatus configured to obtain a tomogram of a fundus of an eye to be examined; and a processing apparatus according to claim 26.

28. The system according to claim 27, further comprising a processor-implemented determination unit which is configured to extract the macular region and the optic nerve papillary region from an image of the fundus of the eye to be examined, and which is configured to determine the line that couples the macular region and the optic nerve papillary region based on the extraction.

29. The system according to claim 28, wherein the line that couples, in the fundus, the macular region and the optic nerve papillary region, is a line that couples, in the fundus, a center of the macular region and a center of the optic nerve papillary region, and wherein the determination unit extracts the center of the macular region and the center of the optic nerve papillary region from the image of the fundus of the eye to be examined.

30. The system according to claim 27, wherein the display unit displays the information indicating the difference at the symmetrical positions with respect to the line that couples the macular region and the optic nerve papillary region.

31. The system according to claim 27, wherein the line that couples, in the fundus, the macular region and the optic nerve papillary region, is a line that couples, in the fundus, a center of the macular region and a center of the optic nerve papillary region.

32. The system according to claim 27, further comprising a processor-implemented determination unit configured to determine automatically the symmetrical positions with respect to the line that couples, in the fundus, the macular region and the optic nerve papillary region.

33. The system according to claim 27, wherein the values regarding layer thicknesses at symmetrical positions include an average value.

34. The apparatus according to claim 26, wherein the values regarding layer thicknesses at symmetrical positions include an average value.

35. A processing apparatus for use in tomography, the processing apparatus comprising:

a processor-implemented comparison unit configured to compare, based on a volume data including a plurality of tomograms obtained using optical coherence tomography, values regarding layer thicknesses at symmetrical positions with respect to a line that couples, in a fundus, a macular region and an optic nerve papillary region; and a display control unit configured to cause a display unit to display, on a two-dimensional image indicating two-dimensional positional relations of the symmetrical positions, information indicating a comparison result by the comparison unit, wherein the comparison unit automatically obtains, as the comparison result, a difference between the values regarding layer thicknesses at symmetrical positions with respect to the line that couples the macular region and the optic nerve papillary region, wherein the display control unit causes the display unit to display as the information indicating a comparison result, using an appearance in accordance with the difference between the values regarding layer thicknesses at symmetrical positions with respect to the line that couples the macular region and the optic nerve papillary region, the information indicating the difference between the values regarding layer thicknesses at symmetrical positions with respect to the line that couples the macular region and the optic nerve papillary region, and wherein the appearance is color, pattern type, or density.

36. The apparatus according to claim 35, wherein the values regarding layer thicknesses at symmetrical positions include an average value.

* * * * *